US005800685A

United States Patent [19]

Perrault

[11] Patent Number: 5,800,685
[45] Date of Patent: Sep. 1, 1998

[54] ELECTRICALLY CONDUCTIVE ADHESIVE HYDROGELS

[75] Inventor: James J. Perrault, Vista, Calif.

[73] Assignee: Cardiotronics Systems, Inc., Carlsbad, Calif.

[21] Appl. No.: 738,651

[22] Filed: Oct. 28, 1996

[51] Int. Cl.$^6$ .................................................. C25B 11/04
[52] U.S. Cl. ........................ 204/291; 252/500; 128/640;
128/798; 128/802; 128/803; 424/484; 424/486;
514/944
[58] Field of Search ........................ 204/291; 252/500;
128/640, 798, 802, 803; 424/484, 486;
514/944

[56] References Cited

U.S. PATENT DOCUMENTS

| | | | |
|---|---|---|---|
| Re. 31,454 | 12/1983 | Hymes | 128/641 |
| 3,929,741 | 12/1975 | Laskey | 260/79.3 M |
| 4,125,110 | 11/1978 | Hymes | 128/2.06 |
| 4,181,752 | 1/1980 | Martens et al. | 427/54.1 |
| 4,259,411 | 3/1981 | Windhager et al. | 428/511 |
| 4,306,996 | 12/1981 | Windhager | 252/500 |
| 4,391,278 | 7/1983 | Cahalan et al. | 128/640 |
| 4,539,996 | 9/1985 | Engel | 128/640 |
| 4,674,512 | 6/1987 | Rolf | 128/640 |
| 4,699,146 | 10/1987 | Sieverding | 128/640 |
| 4,777,954 | 10/1988 | Keusch et al. | 128/640 |
| 4,816,508 | 3/1989 | Chen | 524/300 |
| 4,842,768 | 6/1989 | Nakao et al. | 252/500 |
| 4,848,353 | 7/1989 | Engel | 128/640 |
| 4,947,847 | 8/1990 | Nakao et al. | 128/640 |
| 5,080,097 | 1/1992 | Eisenberg | 128/419 |
| 5,205,297 | 4/1993 | Montecalvo et al. | 128/798 |
| 5,264,249 | 11/1993 | Perrault et al. | 427/327 |
| 5,354,790 | 10/1994 | Keusch et al. | 523/300 |
| 5,402,884 | 4/1995 | Gilman et al. | 206/328 |
| 5,420,197 | 5/1995 | Lorenz et al. | 525/54.3 |
| 5,466,256 | 11/1995 | McAdams et al. | 607/142 |
| 5,520,180 | 5/1996 | Uy et al. | 128/640 |
| 5,525,356 | 6/1996 | Jevne et al. | 424/484 |
| 5,533,971 | 7/1996 | Phipps | 604/20 |

FOREIGN PATENT DOCUMENTS

| | | |
|---|---|---|
| 0 085327 | 1/1983 | European Pat. Off. |
| WO95/27530 | 10/1995 | WIPO |

OTHER PUBLICATIONS

"Chloride Ion Conductivity in a Plasticized Quaternary Ammonium Polymer," Leslie C. Hardy and Duward F. Shriver, Macromolecules, 1984, vol. 17, No. 4, pp. 975–977.

"Hydrogel Electrodes in Biosignal Recording," J. Jossinet and E. McAdams," Annual International Conference of the IEEE Engineering in Medicine and Biology Society, vol. 12, No. 4, 1990, pp. 1490–1491.

"Surface Biomedical Electrode Technology," E. McAdams, International Medical Device & Diagnostic Industry, Sep./Oct. 1990, pp. 44–48.

Jevne, Allan H., Amphoteric N-Substituted acrylamide hydrogel and method, US 5525356A, Jun. 11, 1996, pp. 9–14.

Primary Examiner—Bruce F. Bell
Attorney, Agent, or Firm—Thorpe, North & Western, L.L.P.

[57] ABSTRACT

A composition providing electrically conductive adhesive hydrogels suitable for use as skin contact adhesives and, particularly, suitable for use as an electrical interface for disposable medical devices. The hydrogels are cationic acrylates and may be, for example, preferably made from acrylic esters of quaternary chlorides and/or sulfates or acrylic amides of quaternary chlorides. The present hydrogels are formed by free radical polymerization in the presence of water, preferably by ultra-violet curing with initiator and multi-functional cross-linking agent. The present hydrogels also preferably include a buffer system to help prevent discoloration of the hydrogels and/or hydrolysis of the hydrogels and/or improve shelf-life. Other additives may be added to the present hydrogels either before or after curing (i.e. conductivity enhancers, pharmaceuticals, humectants, plasticizers, etc.) depending on intended end-use. The present hydrogels hydrate a subject's skin, readily wet around a subject's skin surface hair (e.g. chest hair), and protect against burning of a subject upon or due to electrical stimulation through the hydrogel. In addition, the present hydrogels are sufficiently cohesive to enable direct hydrogel-to-hydrogel contact and storage (i.e. without a barrier therebetween), yet remain readily separable. Furthermore, the present hydrogels may be presented in a formula which is non-corrosive to aluminum in contact therewith, and pass standards testing for biocompatibility and electrical properties as developed by the Association for the Advancement of Medical Instrumentation (AAMI) and accepted by the American National Standards Institute.

26 Claims, No Drawings

ELECTRICALLY CONDUCTIVE ADHESIVE HYDROGELS

FIELD OF INVENTION

The present invention relates to electrically conductive adhesive hydrogels, particularly electrically conductive adhesive hydrogels suitable for use as a skin-contacting electrical interface for medical devices.

BACKGROUND

Presently electrically conductive adhesive solid hydrogels and liquid gels are used in the medical field to provide an electrical interface to the skin of a subject to couple electrical signals in to and/or out of the subject (e.g. for diagnostic and/or monitoring uses) and/or to couple electrical stimulus into the subject (e.g. for treatment and/or preventative uses). However, the present hydrogels and liquid gels are inadequate in various aspects.

Problems of prior hydrogels include problems with their adhesive and/or cohesive strength (i.e. they do not sufficiently adhere to the skin, and/or they are insufficiently cohesive to allow for easy removal, and/or they are adherent to themselves such that they must be physically separated (e.g., by a barrier film) to ensure separability (i.e., no straight face-to-face (gel-to-gel) configurations)). See, e.g., Gilman, et al., U.S. Pat. No. 5,402,884 (a package system providing electrical communication between two hydrogel portions, but still requiring separation of the two hydrogel portions). Additional problems with prior hydrogels include problems with sufficiently hydrating the skin in contact with the hydrogel, and, therefore, problems with sufficiently lowering the skin's electrical resistance thereby frequently resulting in heating to a point of burning the skin upon electrical stimulation. See, e.g., E. McAdams, "Surface Biomedical Electrode Technology," Int'l Med. Device & Diagnostic Indus. pp. 44–48 (September/October 1990). Further problems with prior hydrogels include problems with sufficiently wetting around skin hair, and, therefore, problems with sufficiently contacting the skin (i.e. resulting in insufficient electrical contact) thereby frequently resulting in decreased efficacy of defibrillation and increased incidences of heating to the point of burning the skin upon electrical stimulation and/or problems of requiring preparation of skin surfaces prior to use thereby resulting in slowing the speed of procedures. It has been recognized that another problem with prior hydrogels is that electrical pulses transmitted therethrough to a patient causes hydrolysis of the gel, and that this problem is exacerbated with medical stimulation equipment used for defibrillation and/or cardiac pacing because these types of stimulation equipment usually deliver higher voltages and currents to the patient which increases the rate of hydrolysis. For example, defibrillation equipment typically delivers up to 5,000 volts to the patient at a maximum current of 60 amps, and cardiac pacing equipment commonly delivers up to 300 volts to the patient at a maximum current of 0.2 amps.

Liquid gels experience similar problems and have the additional problem of not retaining a set shape over time due to their fluidity which affects their ease of use and storability, and problems of requiring even more time for clean-up due to their lack of cohesive strength.

Therefore, a new hydrogel which is suitable for use in skin-contact and medical devices, and which addresses and resolves these problems is needed.

SUMMARY OF THE INVENTION

The electrically conductive adhesive hydrogels of the present invention are suitable for use as skin-contact adhesives (i.e. are non-irritating, are sufficiently wet to substantially wet and adhere to skin, and are sufficiently cohesive to be readily removable) and are good electrical conductors suitable for use, for example, in disposable medical devices (i.e. sufficiently contact and wet skin to allow passage of electrical current without substantially adversely affecting hydrogel or skin).

The present hydrogels have unique and improved properties as compared to other conductive hydrogels. More particularly, the present hydrogels are stronger, both adhesively (i.e. with respect to adherence to a subject's skin) and cohesively (i.e. cohesive strength of the gel when removing it from a subject's skin or when separating two hydrogel components in direct contact with each other), than prior hydrogels. Also, when compared to prior hydrogels the present hydrogels more efficiently and more sufficiently hydrate the skin surface to which they are applied, and, therefore, are expected to more efficiently and more sufficiently lower the skin surface's electrical resistance resulting in the generation of less heat and lower incidences of burning upon the passage of electrical current to a subject.

In addition, the present hydrogels more effectively wet around skin hair, and, therefore, more efficiently and more sufficiently contact the skin (i.e. to make more sufficient electrical contact) expectedly resulting in increased efficacy of defibrillation, reduced generation of heat, and reduced burning of subject skin surfaces. Also, the present hydrogels require substantially no preparation of the skin surface prior to use (e.g. no preliminary clipping, shaving, or dermal abrasion necessary), and, therefore, are easier and faster to use than prior hydrogels.

The conductive adhesive hydrogels of the present invention are cationic acrylates and are preferably formed by free radical polymerization in the presence of water (preferably by ultra-violet curing with initiator and multi-functional cross-linking agent). The present hydrogels also preferably include a buffer system to help prevent discoloration and/or hydrolysis of the hydrogels, and/or improve their shelf-life. Other additives may also be added to the present hydrogels either before or after curing (i.e. conductivity enhancers, pharmaceuticals, humectants, plasticizers, etc.). The appropriateness of such additives is generally dependent upon the intended end use of the hydrogels.

It is, therefore, a primary objective of the present invention to provide new skin contact conductive adhesive hydrogels made from cationic acrylates.

It is also an objective of the present invention to provide new skin contact conductive adhesive hydrogels made from the acrylic esters of quaternary chlorides and quaternary sulfates.

It is another objective of the present invention to provide new skin contact conductive adhesive hydrogels made from the acrylic amides of quaternary chlorides.

It is a further object of the present invention to provide new skin contact conductive adhesive hydrogels made by free radical polymerization of cationic acrylates in the presence of water.

It is an additional object of the present invention to provide new skin contact conductive adhesive hydrogels formed by the free radical polymerization of cationic acrylates in the presence of water by ultra-violet curing with initiator and multi-functional cross-linking agent (e.g. di- or tri-acrylate cross-linking agent, etc.).

It is another object of the present invention to provide new skin contact conductive adhesive hydrogels which are made from cationic acrylates and which include a buffer system in the hydrogel.

It is a further object of the present invention to provide new skin contact conductive adhesive hydrogels which substantially protect against burning of a subject upon or due to electrical stimulation through the same.

It is yet another object of the present invention to provide new skin contact conductive adhesive hydrogels which are made from cationic acrylates and which can be physically arranged and/or stored in a face-to-face (i.e. hydrogel-to-hydrogel) configuration without a barrier therebetween, and yet remain readily separable.

Other objects and features of the present invention will become apparent from consideration of the following description in conjunction with the accompanying claims.

DETAILED DESCRIPTION OF THE PREFERRED EMBODIMENT

As is set forth above, the present invention relates to conductive and adhesive hydrogels which are suitable to interface electrical signals and/or stimuli between medical devices and subject skin surfaces (i.e. suitable to pass electrical current and suitable to contact skin surfaces for passing electrical current). The present hydrogels preferably have resistivities (or volume resistivities) less than about 20,000 Ωcm at 10 Hz, more preferably have resistivities less than about 10,000 Ωcm at 10 Hz, and even more preferably have resistivities less than about 2,500 Ωcm at 10 Hz, wherein resistivity (or volume resistivity) is defined as equal to:

$$\frac{\text{Resistance } (\Omega) \times \text{Area } (\text{cm}^2)}{\text{Thickness } (\text{cm})}$$

As is also explained above, the hydrogels of the present invention are preferably made from cationic acrylates, examples of which include, but are not limited to, acrylic esters of quaternary chlorides and/or sulfates, and/or acrylic amides of quaternary chlorides.

Cationic acrylates were, until now, believed to make less effective skin contact adhesives perhaps due to a belief that negatively charged polymers would adhere better to skin or would be less irritating to the skin. However, it has been discovered by the present applicant that hydrogels comprising cationic acrylates (i.e. positively charged polymers) exhibit many positive features substantially missing from presently (and previously) used hydrogels.

Particularly, the present cationic acrylate hydrogels are stronger, both adhesively (i.e. removably adherent to a subject's skin) and cohesively (i.e. cleanly removable from a subject's skin), than prior hydrogels. Also, when compared to prior hydrogels the present cationic acrylate hydrogels more efficiently and more sufficiently hydrate a subject's skin surface to which they are applied, and, therefore, expectedly more efficiently and more sufficiently lower the skin surface's electrical resistance resulting in lower generation of heat and lower incidence of burning upon electrical stimulation. In addition, the present hydrogels more effectively wet around skin hair, and, therefore, more sufficiently contact a subject's skin (i.e. to make a more sufficient electrical contact) expectedly resulting in increased efficacy of defibrillation and reduced heating and burning of skin surfaces and, generally, requiring no preparation of the skin surface prior to use. Also, the present hydrogels have been found to be non-irritating to the skin.

Furthermore, the present hydrogels are bactericidal, fungicidal, and resistant to breakdown problems due to exposure to radiation for sterilization purposes.

Another benefit of the present hydrogels not observed in previous hydrogels, is that the present hydrogels may be arranged and stored in face-to-face (i.e. hydrogel-to-hydrogel) contact, substantially without barriers, yet remain readily separable. As is indicated above, previous hydrogels tend to flow together when stored in direct face-to-face configurations (i.e., without barriers), making separation difficult to impossible.

The preferred chemical formula for cationic acrylates suitable for the present invention is shown in Equation 1 wherein $R_1$, $R_2$, $R_3$, $R_4$, and $R_5$ are hydrogen or hydrocarbon groups and wherein $X^-$ is an anion. The preferred method for making such cationic acrylates suitable for the present invention is described below.

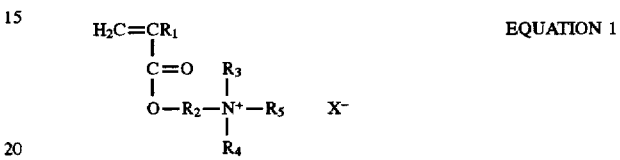

EQUATION 1

Generally, the present hydrogel preferably includes between about 15–60% by weight polymer, more preferably between about 20–50% by weight polymer, and even more preferably between about 25–40% by weight of polymer, with the balance being water. The present hydrogel also preferably includes sufficient buffer to maintain the pH of the hydrogel in a range of about 4.0–5.5. Other additives may also be included.

Specific examples of specific cationic acrylates which the inventor has found presently readily commercially available are shown in Equations 2, 3, and 4 which, respectively, show acryloyloxyethyltrimethyl ammonium chloride which is readily available from CPS Chemical Co. (New Jersey) or Allied Colloid (U.K.), acryloyloxyethyltrimethyl ammonium methyl sulfate which is also readily available from CPS Chemical Co. or Allied Colloid, and acrylamidopropyltrimethyl ammonium chloride which is readily available from Stockhausen (Germany). The preferred process for making these specific examples is described in detail below.

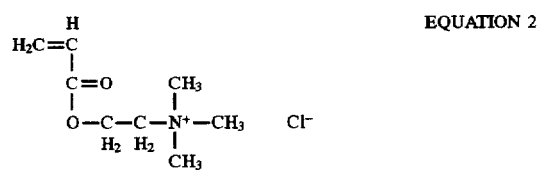

EQUATION 2

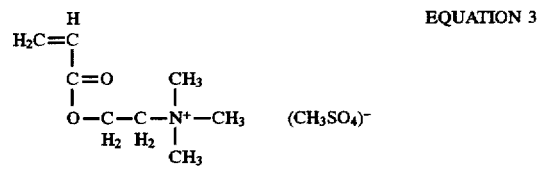

EQUATION 3

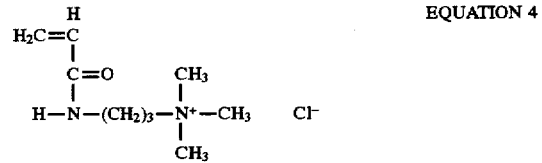

EQUATION 4

The cationic acrylate hydrogels suitable for the present invention are preferably formed by in-situ free radical polymerization of a water soluble monomer (such as those shown above) in the presence of water, preferably by ultraviolet curing with initiator(s) and multi-functional cross-linking agent(s). For example, an appropriate acrylate monomer (as shown in Equation 1), water, optional additional conductor(s) (e.g. salt, for example, sodium chloride, potassium chloride, etc.), initiator or catalyst (e.g. 1-hydroxycyclohexylphenol ketone, etc.), and multifunctional cross-linker (e.g. methylene-bis-acrylamide, etc.) are combined, placed in a mold, and exposed to ultraviolet radiation as is known in the art. The result is a cationic acrylate hydrogel suitable for the present invention which is somewhat clear in color, viscous, and tacky to the touch. The hydrogel tends to be sufficiently adhesive to a subject's skin, yet sufficiently cohesive to be easily removable from the subject's skin and separable from itself.

Examples of co-monomers which may be used with the present invention include co-monomers soluble in water, and, even more preferably include anionic co-monomers so soluble. The amount of co-monomer to be used is in the range of 5–30% by weight, preferably 7–15% by weight, based on the amount of reactants used. Examples of suitable co-monomers include: unsaturated organic carboxylic acids such as acrylic acid, methacrylic acid, maleic acid, itacomic acid, and citraconic acid and salts thereof, unsaturated organic sulfonic acids such as styrene sulfonic acid, methallyl sulfonic acid, 2-sulfoethyl acrylate, 2-sulfoethyl methacrylate, 3-sulfopropyl acrylate, 3-sulfopropyl methacrylate, acrylamide-2-methylpropane sulfonic acid and salts thereof, N,N-dimethylacrylamide, vinyl acetate, other radically polymerizable ionic monomers containing a carbon-carbon double bond, and non-N-vinyl lactam comonomers useful with N-vinyl lactam monomeric units such as N-vinyl-2-pyrrolidone, N-vinyl-2-valerolactam, N-vinyl-2-caprolactam, and mixtures thereof. Among the ionic monomers enumerated above, particularly desirable selections are 3-sulfopropylacrylate or methocrylate, salts thereof, and 2-acrylamide-2-methyl propane sulfonic acid, and salts thereof. Examples of cations involved in the formation of such salts include sodium, potassium, lithium, and ammonium ions. The ionic monomers may be used singly or in a mixture of two or more monomers.

As is mentioned above, the present hydrogels preferably include a buffer system to help control the pH, help prevent discoloration, and/or help prevent breakdown due to the extended presence of water (i.e. help prevent hydrolysis). Buffers, if any, are preferably added to the mixture prior to curing. Suitable buffers include, for example, but are not limited to, sodium potassium tartarate, and/or sodium phosphate monobasic, both of which are commercially readily available from, for example, Aldrich Chemical Co., Inc. The use of a buffer system with the present hydrogel is preferred to provide the hydrogel with a commercially suitable shelf-life (i.e. a shelf-life of over one year) without discoloration.

In addition, the use of buffers also helps prevent electrochemical burning of a subject by helping prevent pH changes and/or shifts as current is driven through a pair of hydrogel electrodes. Typically, in prior systems, as current is driven through a pair of hydrogel electrodes, one electrode becomes more acidic (i.e. its pH decreases) which the other electrode becomes more basic (i.e. its pH increases). This pH shifting problem is particularly prevalent if current is driven through such electrodes for a long period of time (e.g., over 1 hour), such as, for example, during a procedure wherein a patient's heart is being paced. The preferred use of a buffer system as is suggested in the present invention helps buffer against such pH changes as current is driven therethrough and thereby enables use of the electrodes made from the present hydrogel for long periods (e.g. over 24 hours) without electro-chemical burning.

Therefore, it is preferred that buffer be included in the hydrogel to stabilize the cationic polymer, to avoid hydrolysis of the hydrogel, and to avoid pH shifts due to the passage of direct current through the hydrogel. Buffers also help prevent corrosion of metal conductors and are also conductivity enhancers themselves. Some buffers also prevent undesirable yellowing of the hydrogel. The quantity of buffer preferred is preferably between that amount necessary to maintain the monomer solution within a preferred pH range of, for example, about 4.0–5.5, and the highest amount possible which maintains the monomer solution within such a preferred pH range.

As is also mentioned above, other additives may be included in the present hydrogels either before or after curing (i.e. conductivity enhancers, pharmaceuticals, humectants, plasticizers, etc.). The appropriateness of such additives is generally dependent upon the intended end use of the particular hydrogel.

The addition of conductivity enhancers may be preferred even though the hydrogel of the present invention is a polyelectrolyte ionically disassociated in water and, therefore, conductive. In utility, a lower specified quantity of polyelectrolyte (and a correspondingly lower viscosity) may be desired in situations such as, for example, when the hydrogel must wet around chest hair. In such cases, addition of a conductivity enhancer may be useful.

Preferred conductivity enhancers are salts such as potassium chloride and sodium chloride. These salts are preferred since human bodies use these salts for conduction. Although chlorides tend to retard the polymerization of anionic polyelectrolytes, it has been discovered that increasing the concentrations of chlorides enhances the polymerization reactions of the present cationic polyelectrolytes. Additional examples of salts which may be appropriate are lithium chloride, lithium perchlorate, ammonium chloride, calcium chloride, and/or magnesium chloride. Other chloride salts, iodide salts, bromide salts, and/or halide salts may also be suitable.

Other salts, such as salts of weak organic acids, may be preferable. These salts are compatible with human bodies and with the chemistry of the present hydrogel invention, and may be used as conductivity enhancers where the preferred chloride salts might interfere (i.e. corrode) aluminum and/or stainless steel metal components used to interface the hydrogel with medical equipment. Examples of salts which may be suitable, include sodium citrate or magnesium acetate.

While, as is noted above, use of a conductivity enhancer is optional, the amount of conductivity enhancer in a hydrogel is preferably in the range of none to some amount which will enhance the conductivity of the hydrogel, which may be, for example, in the range of about 0–15% by weight.

As is mentioned above, initiators are preferably used in the polymerization of the present hydrogels. Examples of initiators which may be used include, for example, IRGACURE® 184 (1-hydroxycyclohexyl phenyl ketone) and DAROCURE® 1173 (α-hydroxy-α,α-dimethylacetophenone) which are both commercially available from Ciba-Geigy Corp. These UV catalysts are preferred because they are non-yellowing. Other initiators which maintain the preferred water-white and water-clear appearance of the present hydrogels are preferred. However, additional examples of initiators (which may be photo initiators or thermal initiators) may include benzoyl peroxide, azo-bis-isobutyro-nitrile, di-t-butyl peroxide, bromyl peroxide, cumyl peroxide, lauroyl peroxide, isopropyl percarbonate, methylethyl ketone peroxide, cyclohexane peroxide, t-butylhydroperoxide, di-t-amyl peroxide, dicumyl peroxide, t-butyl perbenzoate, benzoin alkyl ethers (such as benzoin, benzoin isopropyl ether, and benzoin isobutyl ether), benzophenones (such as benzophenone and methyl-o-benzoyl benzoate), actophenones (such as acetophenone, trichloroacetophenone, 2,2-diethoxyacetophenone, p-t-butyltrichloro-acetophenone, 2,2-dimethoxy-2-phenyl-acetophenone, and p-dimethylaminoacetophenone), thioxanthones (such as xanthone, thioxanthone, 2-chlorothioxanthone, and 2-isopropyl thioxanthone), benzyl 2-ethyl anthraquinone, methylbenzoyl formate, 2-hydroxy-2-methyl-1-phenyl propane-1-one, 2-hydroxy-4'-isopropyl-2-methyl propiophenone, α-hydroxy ketone, tetramethyl thiuram monosulfide, allyl diazonium salt, and combinations of camphorquinone and ethyl 4-(N,N-dimethylamino) benzoate. Other initiators may be found in, for example, Berner, et al., "Photo Initiators—An Overview", J. Radiation Curing (April 1979), pp. 2–9.

The amount of initiator is preferably within the range of about 0.02–2.0% by weight based on total amount of monomer, and more preferably within the range of about 0.05–0.5% by weight based on total amount of monomer.

UV curing parameters to achieve desired polymer properties are well known to those skilled in the art. An initiator for the present purposes tends to operate by absorbing select wavelengths of UV light, and breaking down into free radicals to initiate polymerization. The wavelengths and curing area set the style of UV bulb used in the curing process. Inhibition of polymerization due to dissolved oxygen, monomer preservatives, or other components may be overcome by changing the power, by pulsing, and/or by using catalyst accelerators. The amount of residual monomer (after polymerization) is preferred to be less than about 3% for good biocompatibility.

As is also noted above, cross-linking agents are preferably used to cross-link the present hydrogels. Examples of multi-functional cross-linking agents which may be used include, for example, methylene-bis-acrylamide and diethylene glycol diacrylate which are both commercially available from, for example, Polysciences, Inc. Warrington, Pa. Additional examples of cross-linking agents which may be acceptable for use in the present invention include ethylene glycol diacrylate, triethylene glycol-bis-methacrylate, ethylene glycol-bis-methacrylate, ethylene glycol-dimethacrylate, bisacrylamide, triethyleneglycol-bis-acrylate, 3,3'-ethylidene-bis(N-vinyl-2-pyrrolidone), trimethylolpropate trimethacrylate, glycerol trimethacrylate, polyethylene glycol dimethacrylate, and other polyacrylate and polymethacrylate esters.

The amount of cross-linking agent is preferably within the range of about 0.02–2.0% by weight based on total amount of monomer, and more preferably within the range of about 0.05–0.5% by weight based on total amount of monomer.

We will now turn to specific exemplary embodiments of cationic acrylate hydrogels of the present invention.

EXAMPLE 1

1. 40.1% Monomer (80% Acryloyloxyethyltrimethyl Ammonium Chloride in water)

2. 40.1% Electrolyte (10% Potassium Chloride in water)

3. 11.8% Crosslinking Solution (0.5% Methylene-Bis-Acrylamide in water)

4. 2.4% Catalyst Solution (3% Hydroxycyclohexyl Phenyl Ketone in Iso-Propyl Alcohol)

5. 5.6% Buffer (Sodium Phosphate Monobasic Monohydrate powder)

These starting materials were mixed in the order given above and placed under a Fusion Systems 600 Watt Continuous UV Lamp. Temperature was 50° C. and pH was 4.2. The following table provides the UV exposure.

| Wavelength | Total Dosage (J/cm$^2$) | Peak Intensity (W/cm$^2$) |
|---|---|---|
| UVA (320–390 nm) | 19 | 1.8 |
| UVB (280–320 nm) | 6.5 | 0.6 |
| UVC (250–260 nm) | 0.3 | 0.03 |
| UVV (395–445 nm) | 9.0 | 0.8 |

The resulting gel had good adhesive and cohesive strength with little residue. It had viscoelastic properties and chemical affinity sufficient to wet around thick chest hair when coated over 200 mils (thousands of an inch) thick. The resulting gel was tested and passed standards testing for biocompatibility and electrical properties as developed by the Association for the Advancement of Medical Instrumentation (AAMI) and accepted by the American National Standards Institute.

EXAMPLE 2

1. 42.0% Monomer (80% Acryloyloxyethyltrimethyl Ammonium Chloride in water)

2. 52.5% Electrolyte (10% Potassium Chloride in water)

3. 4.2% Crosslinking Solution (1% Methylene-Bis-Acrylamide in water)

4. 0.3% Catalyst Solution (3% Hydroxycyclohexyl Phenyl Ketone in Dimethyl Sulfoxide)

5. 1.0% Buffer (Sodium Phosphate Monobasic powder)

These starting materials were mixed in the order given above. The pH was 4.5. The following table provides the UV exposure.

| Wavelength | Total Dosage (J/cm$^2$) | Peak Intensity (W/cm$^2$) |
|---|---|---|
| UVA (320–390 nm) | 5 | 2 |
| UVB (280–320 nm) | 2 | 0.7 |
| UVC (250–260 nm) | 0.15 | 0.05 |
| UVV (395–445 nm) | 2.2 | 1 |

The resulting gel was strong adhesively and cohesively with little residue.

EXAMPLE 3

1. 46.7% Monomer (80% Acryloyloxyethyltrimethyl Ammonium Methyl Sulfate in water)

2. 41.5% Electrolyte (5% Aluminum Potassium Sulfate Dodecahydrate in water)

3. 10.4% Crosslinking Solution (1% Methylene-Bis-Acrylamide in water)

4. 0.4% Catalyst Solution (3% Hydroxycyclohexyl Phenyl Ketone in Dimethyl Sulfoxide)

5. 1.0% Buffer (50% Sodium Hydroxide in water)

These starting materials were mixed in the order given above. The pH was 5.5. The UV exposure is the same as was used for Example 2 above (see table above). The resulting gel had good adhesive and cohesive strength.

EXAMPLE 4

1. 28.7% Monomer (80% Acryloyloxyethyltrimethyl Ammonium Chloride in water)

2. 61.0% Electrolyte (20% Potassium Chloride in water)

3. 9.0% Crosslinking Solution (0.5% Methylene-Bis-Acrylamide in water)

4. 0.3% Catalyst Solution (3% Hydroxycyclohexyl Phenyl Ketone in Dimethyl Sulfoxide)

5. 1.0% Buffer (Potassium Sodium Tartrate powder)

These starting materials were mixed in the order given. The pH was 5.5. The following table provides the UV exposure.

| Wavelength | Total Dosage (J/cm$^2$) | Peak Intensity (W/cm$^2$) |
| --- | --- | --- |
| UVA (320–390 nm) | 9.0 | 2 |
| UVB (280–320 nm) | 2.5 | 0.7 |
| UVC (250–260 nm) | 0.15 | 0.05 |
| UVV (395–445 nm) | 4.8 | 1 |

The resulting gel was soft and very elastic and moist to the touch. Adhesive and cohesive levels were adequate to not leave a residue upon removal. When coated 200 mils thick, material could wet around chest hair and hydrate skin. The gel's ability to hydrate skin was compared to other currently available gels.

The following table provides readings which were taken with a Nova DPM meter one minute after removal of the listed gel from the skin. The quantity is Nova conductance units of improvement over a dry occlusive patch.

| GEL | IMPROVEMENT (Nova conductance units) |
| --- | --- |
| Physio Control Quik Combo | 23 |
| 3M Defib Pads | 24 |
| Example 4 | 263 |

Electrical performance testing was conducted on several different hydrogel electrode pairs comprising the hydrogels of the above-examples. Each electrode of the tested pairs were sized at about 90 cm$^2$ and had a thickness of about 0.4 cm. As is shown in the table below, the hydrogels performed well.

| | ELECTRODE PAIR HYDROGEL | | | | |
| --- | --- | --- | --- | --- | --- |
| TEST | DF39 SPEC (max) | Ex. 1 Gel with Sn Electrode | Ex. 2 Gel with Sn Electrode | Ex. 3 Gel Buffed Al Electrode | Ex. 4 Gel with Sn Electrode |
| DC Offset Voltage | 100 mV | 2.2 mV | 0.4 mV | 6.2 mV | 0.3 mV |
| AC Small Signal Impedance @ 10 Hz | 2000Ω | 12Ω | 1Ω | 30Ω | 1Ω |
| Noise | 150 μV | 2 μV | 0 μV | 0 μV | 0 μV |
| DC Large Signal Impedance | 2Ω | 0.2Ω | 0.2Ω | 0.4Ω | 0.1Ω |
| Actual Defib Recovery: | | | | | |
| 4 Sec. | 400 mV | −126 mV | −97 mV | +59 mV | +9.4 mV |
| 60 Sec. | 300 mV | −57 mV | −42 mV | −23 mV | +1.7 mV |
| Bias Current Maximum: | | | | | |
| DC Offset | 100 mV | −6.0 mV | 1.9 mV | 5.3 mV | 0.5 mV |
| Change from t = 0 | 100 mV | 1.5 mV | −0.5 mV | 7.5 mV | −0.7 mV |

EXAMPLE 5

1. 47.0% Monomer (80% Acryloyloxyethyltrimethyl Ammonium Methyl Sulfate in water)

2. 51.97% Electrolyte (5% Aluminum Potassium Sulfate Dodecahydrate in water)

3. 0.02% Crosslinker (Diethylene Glycol Diacrylate)

4. 0.01% Catalyst (Darocure® 1173)

5. 1.0% Buffer (50% Sodium Hydroxide in water)

A solution was made by mixing components in the order given above. UV exposure is the same as is given above in Example 4. The pH was 5.5 and the curing temperature was 50° C. The resulting gel had good adhesive and cohesive strength with minimal residue. Use of this cross-linker and catalyst saved time as they were liquids that readily dissolved in the monomer solution.

EXAMPLE 6

1. 37.1% Monomer (60% Acrylamidopropyltrimethyl Ammonium Chloride in water)

2. 37.1% Electrolyte (10% Potassium Chloride in water)

3. 23.9% Crosslinking Solution (0.5% Methylene-Bis-Acrylamide in water)

4. 1.5% Catalyst Solution (3% Hydroxycyclohexyl Phenyl Ketone in Dimethyl Sulfoxide)

5. 0.4% Buffer (Citric Acid powder)

These starting materials were purchased or made into solutions in water with the exception of the catalyst which is not directly water soluble. The process and results are the same as in Example 1. The pH was 4.5. The resulting gel was tested and passed AAMI standards testing for biocompatibility and electrical properties.

The electrical performance testing was conducted on a hydrogel electrode pair comprising the Example 6 gel. Each electrode of the tested pairs were sized at about 90 cm$^2$ and had a thickness of about 0.4 cm. As is shown in the table below, the hydrogel performed well.

| | ELECTRODE PAIR HYDROGEL | |
| --- | --- | --- |
| TEST | DF39 SPEC (max) | Ex. 6 Gel w/ Sn Electrode |
| DC Offset Voltage | 100 mV | −5.0 mV |
| AC Small Signal Impedance @ 10 Hz | 2000Ω | 9Ω |
| Noise | 150 μV | 1 μV |
| DC Large Signal Impedance | 2Ω | 0.2 Ω |
| Actual Defib Recovery: | | |
| 4 Sec. | 400 mV | −61 mV |
| 60 Sec. | 300 mV | −24 mV |
| Bias Current Maximum: | | |
| DC Offset | 100 mV | 10.5 mV |
| Change from t = 0 | 100 mV | −8.7 mV |

EXAMPLE 7

1. 23% Monomer (80% Acryloyloxyethyltrimethyl Ammonium Methyl Sulfate in water)

2. 27% Co-Monomer (50% Acrylamidomethylpropanesulfonate, Sodium salt in water)

3. 45% Electrolyte (10% Potassium Chloride in water)

4. 2.5% Crosslinking Solution (1% Methylene-Bis-Acrylamide in water)

5. 2.5% Catalyst Solution (3% Hydroxycyclohexyl Phenyl Ketone in Iso-Propyl Alcohol)

These starting materials were purchased or made into solutions in water with the exception of the catalyst which is not directly water soluble. They were then mixed in the order given above and placed under a Xenon RC500 Pulsed UV lamp for 45 seconds. The exposure time under this equipment is 500 millijoules per square centimeter of ultraviolet light energy. The resulting gel was strong adhesively and cohesively with little residue. The addition of co-monomer improved adhesion over earlier methyl sulfate homopolymer attempts. Other co-monomers could be substituted.

With respect to the initiators (or catalysts) described above, it is known that tertiary amines have been used in the past as accelerants to help accelerate or cure a hydrogel. However, a problem with the use of tertiary amines is that they interfere with ultra violet testing of the resultant polymer (e.g. tests to determine the percent residual monomer) because such tertiary amines absorb ultra violet light. It has been discovered by the present inventor that the use if dimethyl sulfoxide (DMSO) as an accelerant not only helps accelerate curing, but also does not interfere with ultra violet testing of the resulting hydrogel.

The hydrogels of the present invention are particularly suited for use in electronic medical devices such as sensing electrodes which are used for recording or monitoring (e.g. for ECG (electrocardio-gram), EEG (electroencephalogram), and/or EMG (electro-myogram)), or as stimulation electrodes which are used to stimulate a subject (e.g. for transcuteneceous electrical nerve stimulation, for wound healing, for muscle stimulation (e.g. for physical therapy), for external pacing, for defibrillation), or as electro-surgical and/or ablation grounding electrodes, or as electro-transport electrodes (e.g. for the iontophoresis or electrophoresis of drugs into a subject). The hydrogels of the present invention are able to withstand the high voltages and currents of defibrillation and cardiac pacing.

One problem with past such devices is that hydrogels used were not chemically compatible with aluminum or stainless steel (i.e. the hydrogel would cause corrosion of such metal contacting it) or, if the hydrogel did not corrode the metal, it did not pass standards testing for biocompatibility and electrical properties as developed by the Association for the Advancement of Medical Instrumentation (AAMI) and accepted by the American National Standards Institute. Therefore, prior acceptable hydrogel devices used tin electrodes or other metal electrodes. However, use of aluminum electrodes is preferred because such electrodes are radiolucent and, therefore, do not interfere with radio assays of a subject which includes such an electrode whereas electrodes made of tin or other metals do interfere with such assays. The hydrogels of the present invention present a family of hydrogels which do not include chlorides (e.g. see Example 3 above), and which are, therefore, chemically compatible with aluminum and/or stainless steel electrodes contacting the hydrogel.

It should also be noted that while the above specific examples show particular preferred embodiments of the present invention, substitution of the specific constituents of those examples with materials as disclosed herein and as are known in the art made be made without departing from the scope of the present invention. Thus, while embodiments of the present invention have been shown and described, various modifications may be made without departing from the scope of the present invention, and all such modifications and equivalents are intended to be covered.

I claim:

1. An electrically conductive adhesive hydrogel consisting essentially of about 15–60% by weight of a cross-linked cationic polymer prepared by the polymerization of a monomer having the formula:

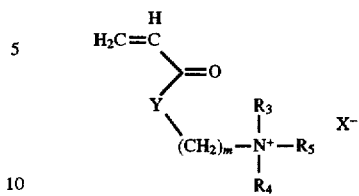

where Y is O or NH, m is 2 or 3, $R_3$, $R_4$ and $R_5$ are either H or $CH_3$ and $X^-$ in an anion and water.

2. The hydrogel of claim 1 wherein the polymer has the formula

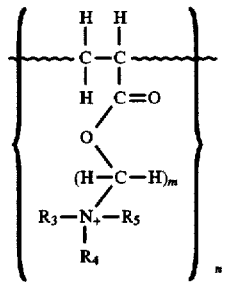

wherein m is 2 or 3, $R_3$, $R_4$, and $R_5$ are selected from the group consisting of hydrogen and $CH_3$, and n is a number greater than 50,000.

3. The hydrogel of claim 2 wherein m is 2 and $R_3$, $R_4$ and $R_5$ are each $CH_3$.

4. The hydrogel of claim 2 wherein the monomer polymerized is acrylamidopropyltrimethyl ammonium chloride.

5. The hydrogel of claim 1, wherein the polymer has the formula

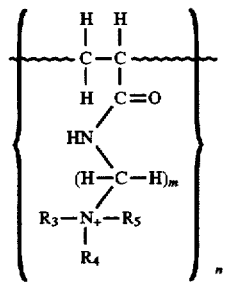

wherein m is 2 or 3, $R_3$, $R_4$, and $R_5$ are selected from the group consisting of hydrogen and $CH_3$, and n is a number greater than 50,000.

6. The hydrogel of claim 5 wherein m is 3 and $R_3$, $R_4$ and $R_5$ are each $CH_3$.

7. The hydrogel of claim 1 where $X^-$ is a chloride or sulfate anion.

8. The hydrogel of claim 1 comprising about 20–50% by weight of said cross-linked cationic acrylate polymer.

9. The hydrogel of claim 1 comprising about 25–40% by weight of said cross-linked cationic acrylate polymer.

10. The hydrogel of claim 1 further comprising up to about 10% by weight of a buffer.

11. The hydrogel of claim 10 wherein the buffer is selected from the group consisting of sodium phosphate monobasic and sodium tartarate.

12. The hydrogel of claims 1 or 10 further comprising up to about 15% by weight of a conductivity enhancer.

13. The hydrogel of claim 12 wherein the conductivity enhancer is selected from the group consisting of a salt.

14. The hydrogel of claim 1 wherein the monomer polymerized is acryloyloxyethyltrimethyl ammonium chloride.

15. The hydrogel of claim 1 wherein the monomer polymerized is acryloyloxyethyltrimethyl ammonium methyl sulfate.

16. The hydrogel of claim 1 wherein the polymer is formed by free radical polymerization in the presence of water.

17. The hydrogel of claim 1 wherein the polymer is formed by ultra violet curing in the presence of an initiator and crosslinking agent.

18. The hydrogel of claim 17 wherein the initiator is selected from the group consisting of hydroxycyclohexyl phenol ketone and hydroxy-α,α-dimethylacetophenone.

19. An electrode comprising and electrically conductive adhesive hydrogel consisting essentially of about 15–60% by weight of a cross-linked cationic polymer prepared by the polymerization of a monomer having the formula:

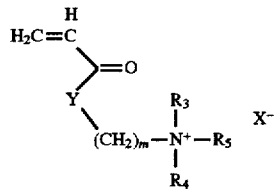

where Y is O or NH, m is 2 or 3, $R_3$, $R_4$ and $R_5$ are either H or $CH_3$ and $X^-$ in an anion and water.

20. The electrode of claim 19 wherein the polymer has the formula

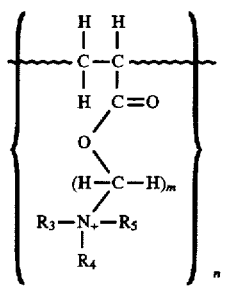

wherein m is 2 or 3, $R_3$, $R_4$, and $R_5$ are selected from the group consisting of hydrogen and $CH_3$, and n is a number greater than 50,000.

21. The electrode of claim 19 wherein the polymer has the formula

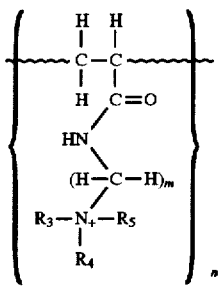

wherein m is 2 or 3, $R_3$, $R_4$, and $R_5$ are selected from the group consisting of hydrogen and $CH_3$, and n is a number greater than 50,000.

22. The hydrogel of claim 19 where $X^-$ is a chloride or sulfate anion.

23. The hydrogel of claim 19 comprising about 20–50% by weight of said cross-linked cationic acrylate polymer.

24. The hydrogel of claim 19 comprising about 25–40% by weight of said cross-linked cationic acrylate polymer.

25. The hydrogel of claim 19 further comprising up to about 10% by weight of a buffer.

26. The hydrogel of claims 19 or 25 further comprising up to about 15% by weight of a conductivity enhancer.

* * * * *